United States Patent [19]

Vertommen et al.

[11] Patent Number: 5,292,839
[45] Date of Patent: Mar. 8, 1994

[54] ALLYL PEROXYKETAL CHAIN TRANSFER AGENTS

[75] Inventors: Luc L. T. Vertommen, Westervoort; John Meijer, Deventer, both of Netherlands; Bernard J. Maillard, Pessac, France

[73] Assignee: Akzo N.V., Arnhem, Netherlands

[21] Appl. No.: 39,253

[22] PCT Filed: Oct. 16, 1991

[86] PCT No.: PCT/EP91/02008
§ 371 Date: Apr. 28, 1993
§ 102(e) Date: Apr. 28, 1993

[87] PCT Pub. No.: WO92/06953
PCT Pub. Date: Apr. 30, 1992

[30] Foreign Application Priority Data

Oct. 16, 1990 [WO] PCT Int'l Appl. ............ PCT/EP90/01780

[51] Int. Cl.$^5$ ................................. C08F 4/32
[52] U.S. Cl. .................... 526/232; 526/232.5; 526/318.4; 526/329.2; 526/335; 526/341; 549/427; 549/501; 560/183; 568/567
[58] Field of Search ............... 568/567; 549/427, 501; 560/183; 526/232, 232.5, 318.4, 329.2, 335, 341

[56] References Cited

U.S. PATENT DOCUMENTS

| | | | |
|---|---|---|---|
| 3,069,474 | 12/1962 | Rieche et al. | 260/610 |
| 3,248,374 | 4/1966 | Covington | 260/78.5 |
| 3,726,832 | 4/1973 | Komatsu et al. | 260/47 |
| 4,176,219 | 11/1979 | Makino et al. | 526/92 |
| 4,405,742 | 9/1983 | Musch et al. | 524/315 |

FOREIGN PATENT DOCUMENTS

| | | |
|---|---|---|
| 0219900 | 4/1987 | European Pat. Off. |
| 0273990 | 7/1988 | European Pat. Off. |
| 0322945 | 7/1989 | European Pat. Off. |
| 8804304 | 6/1988 | PCT Int'l Appl. |
| 9107387 | 5/1991 | PCT Int'l Appl. |

OTHER PUBLICATIONS

International Search Report dated Jan. 31, 1992.
"Alkylated Perepoxides: Peroxonium vs. Phenonium Intermediates from Beta-Haloalkyl tert-Butyl Peroxides and Silver Trifluoroacetate" 1 Org Chem., vol., 51, pp. 1790-1793 (1986).
"An Olefination-Based Route To Unsaturated Hydroperoxides", *Tetrahedron Letters*, vol. 31, No. 36, pp. 5117-5120 (1990).
"Deplacements Homolytiques Intramoleculaires: III—Decomposition Du Peroxyde D'Allyle Et De t-Butyle Dans Les Ethers Et Les Cyclanes: Epoxy-2,3 Propanation De Ces Solvants"; *Tetrahdron Letters*, vol. 41, No. 21, pp. 5039-5043. (1985).

*Primary Examiner*—Joseph L. Schofer
*Assistant Examiner*—Jeffrey T. Smith
*Attorney, Agent, or Firm*—Ralph J. Mancini; Louis A. Morris

[57] ABSTRACT

Novel unsaturated peroxyketals useful as molecular weight regulators in polymerization reactions are disclosed. Also disclosed are a polymerization process employing these novel unsaturated peroxyketals as molecular weight regulators, polymers and oligomers made by this process and articles of manufacture comprising one or more polymers or oligomers made by this process. These molecular weight regulating peroxyketals provide the ability to introduce an epoxy functionality to the oligomer or polymer as well as an additional functionality, in a manner which gives a higher monomer conversion and less by-products than with comparable chain transfer regulators.

7 Claims, No Drawings

ALLYL PEROXYKETAL CHAIN TRANSFER AGENTS

The invention relates to novel allyl peroxyketal chain transfer agents, methods of radically polymerizing monomers in the presence of said peroxyketals to thereby control the molecular weights of the resulting polymers and to polymers and shaped objects containing polymers produced by the instant polymerization methods.

The general concept of employing a molecular weight regulating agent, also known as a chain transfer agent, as an additive during polymerization reactions has been known for a long time. A number of different chain transfer agents having an olefinic group therein, have been employed for this purpose.

Perhaps one of the earlier disclosures of such a polymerization modifying material can be found in U.S. Pat. No. 3,248,374 published on 24 Jun. 1966, wherein the use of an olefin of the formula I as a polymerization modifier is disclosed.

wherein R is hydrogen, halogen or a saturated aliphatic radical and X is halogen, cyanide, phenyl, carboxyl, carbonate, phenyloxy, —CONH$_2$, —CONH-alkyl or —CON-dialkyl. The presence of these olefinic materials during the polymerization of vinylidene chloride with other olefinic materials rendered the resultant polymer more water soluble.

U.S. Pat. No. 3,726,832 published on 10 Apr. 1973, discloses the use of a cyclic ether or a vinyl ether as a molecular weight regulator for the polymerization of dienes.

U.S. Pat. No. 4,176,219 published on 27 Nov. 1979, discloses the use of allyl halides, benzyl halides or a tertiary aliphatic halide compound as molecular weight regulators for the production of 1,2-polybutadiene.

U.S. Pat. 4,405,742, published on 20 Sep. 1983, discloses the use as a regulator, of unsaturated ethers, thioethers, amines, and acrylates and thioacrylates of acrylamides for the purpose of polymerizing chloroprene to produce an improved polychloroprene product.

PCT patent application WO 88/04304 published on 16 Jun. 1988 discloses the use of compounds of the formula (II) for the purpose of controlling the molecular weight and end group functionality of polymers.

wherein R$_1$ is hydrogen or a group capable of activating the vinylic carbon towards free radical addition; Y is OR$_2$ or CH$_2$X(R$_2$)$_n$, where R$_2$ is an optionally substituted alkyl, optionally substituted alkenyl, optionally substituted alkynyl, or optionally substituted saturated or unsaturated carbocyclic or heterocyclic ring; X is an element other than carbon selected from Groups IV, V, VI or VII of the Periodic Table or a group consisting of an element selected from Groups IV, V or VI to which is attached one or more oxygen atoms; and n is a number from 0 to 3 such that the valency of X is satisfied and, when n is greater than 1, the groups represented by R$_2$ may be identical or different.

Finally, PCT patent application WO 91/06535 published on 16 May 1991 discloses the use of compounds of the formula (III) for the purpose of controlling the molecular weight and end group functionality of polymers.

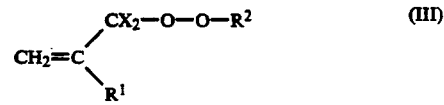

wherein R$^1$ is hydrogen, chlorine, an alkyl group or a group capable of activating the vinylic carbon towards free radical addition; R$^2$ is hydrogen or an optionally substituted alkyl, alkenyl, aryl, cycloalkenyl or cycloalkyl group or the group —COZ, where Z is R$^3$ or OR$^3$, where R$^3$ is hydrogen or an optionally substituted alkyl, alkenyl or aryl group. X is a hydrogen atom, an optionally substituted alkyl, alkenyl halogen, and the two X groups may be the same or different.

The present invention relates to organic peroxides useful as chain transfer agents in radical polymerization of monomers characterized in that said organic peroxides are represented by the following formula:

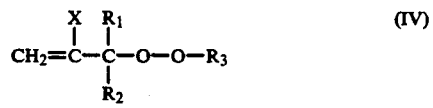

wherein R$_1$ and R$_2$ are independently selected from hydrogen, lower alkyl, alkenyl and aryl; R$_3$ is represented by the formula V:

wherein R$_4$, R$_5$ and R$_6$ are independently selected from optionally substituted lower alkyl, alkenyl, aryl and hydrogen, whereby R$_4$ and R$_5$ cannot be hydrogen together, or any two of R$_4$, R$_5$ and R$_6$ may combine to form a ring; and X is an activating group capable of enhancing the reactivity of the olefinic group towards free radical addition.

The present invention also relates to a polymerization process employing the organic peroxides of the formula IV as chain transfer agents, polymers produced by this polymerization process and shaped objects comprising one or more of such polymers.

Similar peroxides are known from EP 0 322 945 and EP 0 273 990 for use as polymer modification agents. In the processes of these patent applications, however, the unsaturated peroxides are contacted directly with the preformed polymer to thereby introduce functional groups onto the polymer. In addition, these peroxides are significantly different from the present peroxides at least because they do not include an activating group X adjacent the olefinic group.

Tertiary alkenyl peroxy esters are disclosed for use as initiators and curing agents in EP 0 219 900. However, there is no mention of using these materials as chain transfer agents or even of any chain transfer activity.

Further, these compounds differ from those of the present invention at least because they are all esters.

Finally, "Deplacements Homolytiques Intramoleculaires," Tetrahedron, Vol. 41, No. 21, pp. 5039–5043, (1985) discloses the use of unsaturated peroxides for 2,3-epoxypropanating several low molecular weight compounds. The unsaturated peroxides described in this patent again differ from those of the present invention since they do not contain an activating group X adjacent the olefinic group. Further, the epoxypropanation of low molecular weight materials bears little, if any, relation to the application of a material as a chain transfer agent.

The peroxides of the invention correspond to the above-described formula IV. They may be prepared in the usual manner for similar peroxides. In preparing the peroxides of the present invention use may be made of an alkenyl derivative of the general formula:

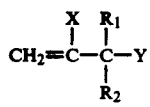

or

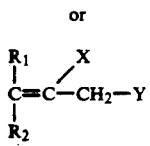

wherein X is an activating group capable of enhancing the reactivity of the olefinic group towards free radical addition, $R_1$ and $R_2$ are independently selected from hydrogen, lower alkyl, alkenyl and aryl and Y is Cl, Br, $OSO_2R$, OH, OOH,

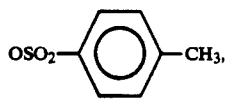

or a different leaving group.

As examples of suitable starting compounds may be mentioned: 2-ethoxy carbonyl-2-propenyl bromide, 2-phenyl-2-propenyl bromide, 2-ethoxy carbonyl-2-propenyl chloride, 2-phenyl-2-propenyl chloride, 2-phenyloxy carbonyl-2-propenyl bromide, 2-carboxy-2-propenyl chloride, 2-acetyloxy-2-propenyl bromide, 2-N,N-dimethylcarbonyl-2-butenyl bromide, 2-cyano-2-propenyl bromide, and 2-ethoxycarbonyl-2-butenyl chloride.

In the preparation of the present peroxides, an alkenyl halide VI or VII can be reacted in the usual way, in an alkaline medium, with a hydroperoxide in the presence of a phase transfer catalyst.

Another useful method for the preparation of the peroxides of the present invention is to first prepare an unsaturated hydroperoxide and then react the unsaturated hydroperoxide with an additional material to thereby introduce the group R3 thereto. Examples of these preparation methods are illustrated by the preparations of:

ethyl-2-(1-(1-methoxyheptylperoxy)ethyl) propenoate from 1-methyl-2-ethoxycarbonyl-2-propenyl hydroperoxide and 1,1-dimethoxy-heptane by transacetalization using p-toluene sulphonic acid, ethyl-2-(1-(1-methoxypropylperoxy)ethyl) propenoate from 1-methyl-2-ethoxycarbonyl-2-propenyl hydroperoxide and 1,1-dimethoxy-propane by transacetalization using p-toluene sulphonic acid, ethyl-2-(1-(1-methoxy-2-methylpropylperoxy)ethyl) propenoate from 1-methyl-2-ethoxycarbonyl-2-propenyl hydroperoxide and 1,1-dimethoxy-2-methyl-propane by transacetalization using p-toluene sulphonic acid, ethyl-2-(1-(1-methoxy-2,2-dimethylpropylperoxy)ethyl) propenoate from 1-methyl-2-ethoxycarbonyl-2-propenyl hydroperoxide and 1,1-dimethoxy-2,2-dimethyl-propane by transacetalization using p-toluene sulphonic acid, ethyl-2-(1-(1-methoxy-1-methylpropylperoxy)ethyl) propenoate from 1-methyl-2-ethoxycarbonyl-2-propenyl hydroperoxide and methylethylketone using p-toluene sulphonic acid in trimethoxy methane, ethyl-2-(1-(1-benzyl-1-methoxyethylperoxy)ethyl) propenoate from 1-methyl-2-ethoxycarbonyl-2-propenyl hydroperoxide and benzyl methyl ketone using p-toluene sulphonic acid in trimethoxy methane, ethyl-2-(1-(1-methoxy-1-cyclohexene-3-ylperoxy)ethyl) propenoate from 1-methyl-2-ethoxycarbonyl-2-propenyl hydroperoxide and 1-methoxy-1,4-cyclohexadiene using p-toluene sulphonic acid, ethyl-2-(1-(2-methyl-2-tetrahydrofuranylperoxy)ethyl) propenoate from 1-methyl-2-ethoxycarbonyl-2-propenyl hydroperoxide and 2-methyl-4,5-dihydrofurane using p-toluene sulphonic acid, ethyl-2-(1-(2-(6-ethoxy)tetrahydropyranylperoxy)ethyl) propenoate from 1-methyl-2-ethoxycarbonyl-2-propenyl hydroperoxide and 2-ethoxy-2,3-dihydropyrane using p-toluene sulphonic acid, ethyl-2-(1-(1-methoxy-1-cyclohexylperoxy)ethyl) propenoate from 1-methyl-2-ethoxycarbonyl-2-propenyl hydroperoxide and 1-methoxy-1-cyclohexylene using p-toluene sulphonic acid, ethyl-2-(1-(1-methoxy-1-cyclopentylperoxy)ethyl) propenoate from 1-methoxy-2-ethoxycarbonyl-2-propenyl hydroperoxide and 1-methoxy-1-cyclopentylene using p-toluene sulphonic acid, ethyl-2-(1-(1-butoxyethylperoxy)ethyl) propenoate from 1-methoxy-2-ethoxycarbonyl-2-propenyl hydroperoxide and butylethylene-ether using p-toluene sulphonic acid, ethyl-2-(1-(2-tetrahydrofuranylperoxy)ethyl) propenoate from 1-methyl-2-ethoxycarbonyl-2-propenyl hydroperoxide and 1-methoxy-tetrahydrofuran using p-toluene sulphonic acid, and ethyl-2-(1-(2-tetrahydropyranylperoxy)ethyl) propenoate from 1-methyl-2-ethoxycarbonyl-2-propenyl hydroperoxide and 1,2-dihydropyrane using p-toluene sulphonic acid in diethylether.

The organic peroxides of the present invention are generally represented by the following formula:

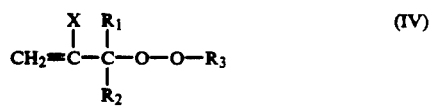

wherein $R_1$ and $R_2$ may be the same or different and are selected from hydrogen, lower alkyl, alkenyl and aryl, or $R_1$ and $R_2$ may combine to form a $C_5$–$C_7$ aliphatic ring, $R_3$ is represented by the formula V:

(V)

wherein $R_4$, $R_5$ and $R_6$ are independently selected from optionally substituted lower alkyl, alkenyl, aryl, and hydrogen, whereby $R_4$ and $R_5$ cannot be hydrogen together, or any two of $R_4$, $R_5$ and $R_6$ may combine to form a ring; and X is an activating group capable of enhancing the reactivity of the olefinic group towards free radical addition, and together with $R_1$ or $R_2$, may combine to form an aliphatic ring. Preferably, $R_4$, $R_5$ and $R_6$ are selected from the group consisting of an alkyl group having 1–10 carbon atoms; an alkenyl group having 2–18 carbon atoms or an aryl group having 6–30 carbon atoms all of which may be optionally substituted with one or more of hydroxyl, amino, epoxy and carboxy groups; hydrogen, whereby $R_4$ and $R_5$ cannot be hydrogen together or any two of $R_4$, $R_5$ and $R_6$ may combine to form a ring. Particular examples of useful $R_4$, $R_5$ and $R_6$ groups include: t-butyl, t-amyl, t-pentyl, t-pentenyl, t-hexyl, t-heptyl, allyl, propenyl, butenyl, pentenyl, phenyl, tolyl, benzyl, hydroxybutyl, carboxyethyl, epoxy methyl, butylamine and propylamine, among others.

X is an activating group capable of enhancing the reactivity of the olefinic unsaturation towards free radical addition. Preferably, X is a group selected from the group consisting of ester, acid, carbonyl, alkoxy carbonyl, alkoxy, phenyl, substituted aromatic, aryloxycarbonyl, carboxy, acyloxy, aryloxy, epoxy, carbamoyl, halogens, halocarbons,

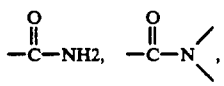

carbonates, sulfones, sulfoxides, phosphonates, phosphine oxides, and cyano or a group including two or more of these functionalities which may be the same or different. X may also combine with $R_1$ or $R_2$ to form a $C_5$–$C_7$ aliphatic ring. In a preferred embodiment X is an electron-withdrawing group optionally having one or more functionalities such as hydroxy, carboxy, epoxy and amino.

The group X may be selected on the basis of its effect on the chain transfer coefficient of the peroxide. More particularly, the ideal chain transfer coefficient is about one. Thus, for a particular peroxide, X can be selected to control the reactivity of the chain transfer agent such that the chain transfer coefficient is as close to one as possible. In this manner, the monomeric starting materials can be added in the ratio in which they are desired in the polymeric products.

As typical examples of the unsaturated peroxides which are useful as chain transfer agents according to the present invention, the following compounds may be mentioned:

Ethyl-2-(1-(1-methoxyheptylperoxy(ethyl) propenoate,
ethyl-2-(1-(1-methoxypropylperoxy(ethyl) propenoate,
ethyl-2-(1-(1-methoxy-2-methylpropyl)peroxyethyl) propenoate,
ethyl-2-(1-(1-methoxy-2,2-dimethylpropylperoxy(ethyl) propenoate,
ethyl-2-(1-(1-methoxy-1-methylpropylperoxy(ethyl) propenoate,
ethyl-2-(1-(1-benzyl-1-methoxyethylperoxy(ethyl) propanoate,
ethyl-2-(1-(1-methoxy-1-cyclohexene-3-ylperoxy(ethyl) propenoate,
ethyl-2-(1-(2-methyl-2-tetrahydrofuranylperoxy(ethyl) propenoate,
ethyl-2-(1-(2-(6-ethoxy)tetrahydropyranylperoxy(ethyl) propenoate,
ethyl-2-(1-(1-methoxy-1-cyclohexylperoxy(ethyl) propenoate,
ethyl-2-(1-(1-methoxy-1-cyclopentylperoxy(ethyl) propenoate,
ethyl-2-(1-(1-butoxyethylperoxy(ethyl) propenoate,
ethyl-2-(1-(2-tetrahydrofuranylperoxy)ethyl) propenoate, and
ethyl-2-(1-(2-tetrahydropyranylperoxy)ethyl) propenoate.

The peroxides can be prepared, transported, stored and applied as such or in the form of powders, granules, solutions, aqueous suspensions, emulsions, pastes or any other known method. Which of these physical forms is preferred will depend on the particular polymerization system being employed. Also, considerations of safety (desensitization) may play a role. Desensitizing agents may, in fact, be used with the peroxides of the present invention and particularly suitable desensitizing agents include solid carrier-materials such as silica, chalk and clay, inert plasticizers or solvents such as mono- or dichloro benzene, and of course water.

The process of the present invention employs compounds of the formula IV as alternatives to known chain transfer agents for the control of molecular weight. The process of the present invention may be operated in the same manner as processes employing conventional chain transfer agents such as thiols. For example, the present process can be used in the manufacture of synthetic rubbers and other polymer formulations, where reduced molecular weight aids polymer processing and improves the polymer properties. The process is also applicable to the production of low molecular weight polymers and oligomers for a variety of applications such as for use in paints or coatings.

The chain transfer agents of the present invention offer several advantages. First, these materials exhibit an unexpectedly good ability to control molecular weights in polymerization processes. Thus, polymers of various molecular weights, with accurate control of the $M_n$, can be obtained. In its simplest form, molecular weight can be regulated simply by varying the amount of peroxide chain transfer agent added to the system.

Secondly, the method of the present invention is extremely versatile as is evidenced by the variety of polymerizations in which molecular weight regulation has been successful.

Thirdly, as a result of the process of the present invention, each polymer chain may be terminated by at least a bifunctional end group. This is the result of the rearrangement of the peroxide functionality to form an epoxy functionality, in combination with the carrying over of the group X from the unsaturated peroxide initiator into the end group of the formed polymer or oligomer. It is also possible to form telechelic polymers by the present process. The process of the present invention is extremely useful in producing omega substituted polymers, as well as alpha, omega disubstituted polymers. These polymers and oligomers produced by the process of the present invention may be grafted onto other polymers or reacted with other monomers, polymers or oligomers to form block copolymers or graft copolymers. Such copolymers have many known uses. The polymers/oligomers produced can also be involved in cross-linking reactions.

An additional advantage of the chain transfer agents of the present invention is that by chain termination of the polymer, a special type of $R_3O$ radicals are liberated. These oxygen-centered radicals readily rearrange to carbon-centered radicals thereby leading to several advantages over comparable chain transfer agents which also liberate oxygen-centered radicals on chain termination.

For example, oxygen-centered radicals add readily to a styrene monomer but do not add readily to acrylate monomers. This results in the retardation of the polymerization, which is observed with comparable chain transfer agents in comparative Examples A and B of the present application. The oxygen-centered radicals released upon chain termination by the peroxyketal chain transfer agents of the present invention readily rearrange to carbon-centered radicals which add to both styrene and acrylate monomers, thereby resulting in a higher monomer conversion when polymerizing these monomers.

Due to the slow addition onto the acrylics and the excellent ability of oxygen-centered radicals to abstract hydrogen, side products are formed by prior art chain transfer agents, which side products result mainly from allylic abstraction on the peroxide, as shown by the incorporation of ethyl acrylate monomer units into the final polymer.

By using the present peroxyketals as chain transfer agents, the oxygen-centered radicals which are liberated provide the advantage that they rearrange to carbon-centered radicals which are not good hydrogen abstractors. Thus, side products from allylic abstraction are minimal.

In addition, the functional end groups on the polymers or oligomers made by the process of the present invention may be changed to other functional groups by known reaction processes. For example, the epoxy functionality may simply be converted to a hydroxy functionality using known methods.

In the present process, one simply carries out the normal polymerization process in the presence of one or more compounds of the formula IV to thereby regulate the molecular weight of the polymer and provide functional end groups on the polymer. The reaction is generally carried out under normal polymerization conditions for the monomer being polymerized.

As an initiator may be used conventional polymerization initiators known in the art. The most preferred initiator will often depend upon the particular monomer which will be polymerized. In the case of styrene or methyl methacrylate polymerizations, the initiator of choice is azobisisobutyronitrile (AIBN). Generally, the amount of initiator used will be determined by known data for the particular polymerization process and will be independent of the type and amount of the chain transfer agent to be employed.

The chain transfer agent itself may be employed in various amounts depending primarily upon the monomer being polymerized, the chain transfer coefficient of the chain transfer agent and the desired molecular weight range to be obtained. As little as 0.001 mole percent of chain transfer agent based on the monomer can be used and up to 30.0 mole percent may also be employed. In general, from 0.1 to 15 mole percent of the chain transfer agent will produce the desired result. Of course, mixtures of different chain transfer agents may also be employed.

It is preferred to select a chain transfer agent which has a decomposition temperature above the polymerization temperature since decomposition of the chain transfer agent will prevent it from acting to regulate molecular weight. However, this need not always be the case. For example, in some instances it may be desirable for the unsaturated peroxide to act as both a chain transfer agent and an initiator, in which case some decomposition of the peroxide will be desirable. Any polymerizable monomer can be used in the process of the present invention. As examples of suitable polymerizable monomers may be mentioned acrylates, methacrylates, styrene, styrene derivatives, vinyl esters, dienes, acrylonitrile, and olefins.

The present invention also relates to the polymers and oligomers which are formed by the process of the invention. In this respect, it has been verified by spectral analyses that these materials include an epoxy functionality as well as the group X. Accordingly, these oligomers and polymers are special because of the many synthetic possibilities offered by the presence of an epoxy group as well as the group X. Finally, the present invention also includes articles of manufacture which comprise one or more polymers or oligomers made by the process of the present invention. These articles of manufacture are useful in the coating industry, as lubricants, processing aids and interfacial agents for polymers, among other uses.

The following examples are presented to further illustrate the present invention.

EXAMPLE 1

Preparation of ethyl-2-(1-(2-tetrahydropyranylperoxy)ethyl) propenoate (ETEP).

A stirred solution of 11.56 g 1-methyl-2-ethoxycarbonyl-2-propenyl hydroperoxide and 0.3 g p-toluene sulphonic acid in 50 ml diethylether was cooled below 0° C. Then 5.04 g of dihydropyrane as a 50 ml solution in diethylether was added drop wise maintaining the temperature below 0° C. The reaction solution was stirred during ½ hour at a temperature below 0° C., followed by another 2 hours at room temperature. Thereafter the reaction solution was washed with 80 ml $K_2CO_3$ in aqueous solution. The organic phase was separated and subsequently dried with $MgSO_4$, after which the diethylether was evaporated. Ethyl-2-(1-(2-tetrahydropyranylperoxy)ethyl) propenoate was obtained in a yield of 70%.

Example 2

Polymerization of styrene, methyl methacrylate (MMA) and butyl acrylate (BA) in the presence of ethyl-2-(1-(2-tetrahydropyranylperoxy)ethyl propenoate (ETEP).

The chain transfer coefficient, mentioned in the following examples, is calculated in the following way. The ratio of the molecular weight $M_n$ to the molecular weight of the monomer M ($M_n$/M) gives DP. 1/DP is plotted against the ratio of the chain transfer agent (CTA) concentration to the monomer concentration ([CTA]/[Monomer]). A straight line is obtained. The slope of the straight line is the chain transfer agent coefficient (Mayo equation).

Styrene Polymerization Method

To a 1.2 molar solution of styrene in o-dichlorobenzene was added 0.5 mol % of AIBN and varying amounts of ETEP. The polymerization was carried out at a temperature of 80° C. over a period of 60 minutes. The results are shown in Table I and include a control polymerization wherein no chain transfer agent was employed. The monomer conversion and molecular weights are given in Table 1. Calculation of the chain transfer coefficient for ETEP for styrene polymerization yielded a value of 0.65.

Methyl Methacrylate Polymerization Method

To a 1.2 molar solution of methyl methacrylate in o-dichlorobenzene was added 0.5 mol % of AIBN and varying amounts of ETEP. The polymerization was carried out at a temperature of 80° C. over a period of 60 minutes. The results are shown in Table 1 and include a control polymerization wherein no chain transfer agent was employed. The monomer conversion and molecular weights for methyl methacrylate polymerization are given in Table 1. Calculation of the chain transfer coefficient for ETEP for methyl methacrylate polymerization yielded a value of 0.17.

Butyl Acrylate Polymerization Method

To a 1.2 molar solution of butyl acrylate in o-dichlorobenzene was added 0.5 mol % of AIBN and varying amounts of ETEP. The polymerization was carried out at a temperature of 80° C. over a period of 60 minutes. The results are Shown in Table 1 and include a control polymerization wherein no chain transfer agent was employed. The molecular weights and monomer conversion are given in Table 1. Calculation of the chain transfer coefficient for ETEP for butyl acrylate polymerization yielded a value of 0.63.

TABLE 1

| [ETEP]/[monomer] | MMA Mon. conv. % | MMA $M_n$ | Styrene Mon. conv. % | Styrene $M_n$ | BA Mon. conv. % | BA $M_n$ |
|---|---|---|---|---|---|---|
| 0 | 52.5 | 20115 | 16.6 | 8013 | 74.4 | 30482 |
| 0.01 | 57.2 | 14375 | 17.7 | 4565 | 72.1 | 8994 |
| 0.02 | 56.3 | 11297 | 14.9 | 3275 | 68.8 | 5448 |
| 0.04 | 50.3 | 8250 | 17.3 | 2311 | 66.1 | 3507 |
| 0.07 | 49.3 | 5605 | 13.6 | 1620 | 59.3 | 2356 |
| 0.10 | 49.2 | 4690 | 17.0 | 1312 | 57.0 | 1856 |

1H- and 13C-NMR showed that formate and epoxy functional groups were introduced in the polymer in a quantative ratio of 1:1.

Comparative Examples A and B

The procedures of Example 2 were repeated with two prior art chain transfer agents and the results, including monomer conversion and molecular weights for styrene, methyl methacrylate (MMA) and butyl acrylate (BA) polymerizations are given in Tables 2 for Comparative Example A and 3 for Comparative Example B. Comparative Example A employed ethyl t-butyl-peroxymethyl propenoate (ETBPMP). Comparative Example B employed 2-ethoxycarbonyl-3-hydroperoxy butene-1 (AHP).

TABLE 2

| [ETBPMP]/[monomer] | MMA Mon. conv. % | MMA $M_n$ | Styrene Mon. conv. % | Styrene $M_n$ | BA Mon. conv. % | BA $M_n$ |
|---|---|---|---|---|---|---|
| 0 | 55.3 | 23533 | 12.4 | 8686 | 41.4 | 21050 |
| 0.01 | 41.0 | 10180 | 11.8 | 2536 | | |
| 0.02 | 35.8 | 6826 | 10.6 | 1692 | 18.7 | 3335 |
| 0.04 | 27.7 | 4336 | 16.5 | 1161 | 14.5 | 2112 |
| 0.06 | 25.1 | 3294 | | | | |
| 0.07 | | | 10.3 | 840 | | |
| 0.1 | 19.0 | 2416 | 10.7 | 705 | | |
| 0.12 | | | | | 9.4 | 1114 |
| 0.16 | | | | | 7.9 | 978 |
| 0.2 | | | | | 6.8 | 880 |

TABLE 3

| [AHP]/[monomer] | Styrene Mon. conv. % | Styrene $M_n$ | BA Mon. conv. % | BA $M_n$ |
|---|---|---|---|---|
| 0 | 13.0 | 8961 | 67.1 | 22262 |
| 0.005 | 13.6 | 5424 | 35.0 | 11218 |
| 0.01 | 12.1 | 4124 | 25.0 | 7909 |
| 0.02 | 11.0 | 2925 | 16.0 | 5111 |
| 0.035 | | | 12.3 | 3500 |
| 0.04 | 11.2 | 2104 | | |
| 0.05 | | | 9.2 | 2816 |
| 0.056 | 10.3 | 1662 | | |

Calculations of the chain transfer coefficient for ETBPMP for methyl methacrylate, styrene and butyl acrylate polymerization yielded values of 0.42, 1.3 and 0.7–1.3, respectively.

Calculations of the chain transfer coefficient for AMP for styrene and butyl acrylate polymerizations yielded values of 0.89 and 0.79, respectively.

The foregoing examples have been presented for the purpose of illustration and description only and are not to be construed as limiting the scope of the invention in any way. The scope of the invention is to be determined by the claims appended hereto.

What is claimed is:

1. Peroxides useful as chain transfer agents in radical (co)polymerization of monomers characterized in that said peroxides are represented by the following formula:

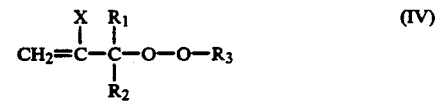

(IV)

wherein $R_1$ and $R_2$ are independently selected from hydrogen, lower alkyl, alkenyl and aryl, or $R_1$ and $R_2$ may combine to form a $C_5$–$C_7$ aliphatic ring: $R_3$ is represented by the formula V:

(V)

wherein $R_4$, $R_5$ and $R_6$ are independently selected from optionally substituted lower alkyl, alkenyl aryl and hydrogen, whereby $R_4$ and $R_5$ cannot be hydrogen together, or any two of $R_4$, $R_5$ and $R_6$ may combine to form a ring; and X is an activating group capable of enhancing the reactivity of the olefinic group towards free radical addition, and together with $R_1$ or $R_2$, may combine to form an aliphatic ring.

2. Peroxides as claimed in claim 1 wherein $R_4$, $R_5$ and $R_6$ are selected from the group consisting of an alkyl group having 1-10 carbon atoms; an alkenyl group having 2-18 carbon atoms or an aryl group having 6-30 carbon atoms, all of which may be optionally substituted with one or ore of hydroxyl, amino, epoxy and carboxy groups; hydrogen, whereby $R_4$ and $R_5$ cannot be hydrogen together, or ny two of $R_4$, $R_5$ and $R_6$ may combine to form a ring.

3. Peroxides as claimed in claim 2 wherein X is a group selected from the group consisting of ester, acid, carbonyl, alkoxy carbonyl, alkoxy, phenyl, substituted aromatic, aryloxycarbonyl, carboxy, acyloxy, aryloxy, epoxy, carbamoyl, halogens, halocarbons,

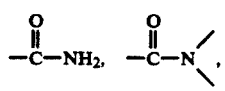

carbonates, sulfones, sulfoxides, phosphonates, phosphine oxides, and cyano or a group including two or more of these functionalities which may be the same or different, or X may combine with $R_1$ or $R_2$ to form a $C_5$-$C_7$ aliphatic ring.

4. Peroxides as claimed in claim 2 wherein X is an electron-withdrawing group substituted with one or more functionalities selected from hydroxy, carboxy, epoxy and amino.

5. In a method of radically (co)polymerizing monomers, the improvement characterized by conducting the polymerization reaction in the presence of an effective amount one or more peroxides as claimed in claim 1 to thereby regulate the molecular weight of the resulting polymer.

6. A method as claimed in claim 5, wherein from 0.001 to 30.0 mole percent of said peroxide based on the moles of polymerizable monomer, is employed.

7. A method as claimed in claim 6 wherein said polymerizable monomer is selected from the group consisting of acrylates, methacrylates, styrene, styrene derivatives, vinyl esters, dienes, acrylonitrile and olefins.

* * * * *

UNITED STATES PATENT AND TRADEMARK OFFICE
CERTIFICATE OF CORRECTION

PATENT NO. : 5,292,839
DATED : March 8, 1994
INVENTOR(S) : VERTOMMEN, Luc, L. T., et al.

It is certified that error appears in the above—identified patent and that said Letters Patent is hereby corrected as shown below:

Column 11, Claim 2, line 6, please change "ore" to -- more --;

Column 11, Claim 2, line 8, please change "ny" to -- any --.

Signed and Sealed this

Twelfth Day of July, 1994

Attest:

BRUCE LEHMAN

Attesting Officer     Commissioner of Patents and Trademarks